United States Patent [19]

Galabov et al.

[11] 4,048,333

[45] Sept. 13, 1977

[54] METHOD FOR TREATING A PICORNA VIRUS INFECTION

[75] Inventors: Angel Simeonov Galabov; Lubomir Mihaylov Shindarov; Georgi Nikolov Vassilev; Ragka Taneva Vassileva; Zlatka Petkova Dimcheva; Dushka Staneva Stoycheva; Emilia Hristova Velichkova, all of Sofia, Bulgaria

[73] Assignee: Medizinska Akademia, Sofia, Bulgaria

[21] Appl. No.: 585,517

[22] Filed: June 10, 1975

Related U.S. Application Data

[63] Continuation of Ser. No. 282,918, Aug. 23, 1972, abandoned.

[30] Foreign Application Priority Data

Aug. 23, 1971  Bulgaria .................................. 17294

[51] Int. Cl.² .................... A61K 31/17; A61K 31/44; A61K 31/34; A61K 31/27
[52] U.S. Cl. ................................. 424/322; 424/263; 424/285; 424/300
[58] Field of Search ........................................ 424/322

[56] References Cited

PUBLICATIONS

Chemical Abstracts 77: 29549m, July 31, 1972.

*Primary Examiner*—Jerome D. Goldberg
*Attorney, Agent, or Firm*—Armstrong, Nikaido & Marmelstein

[57] ABSTRACT

A method of treating picorna viral infections, particularly of the picornaviruses, is provided which comprises treating the patient with an effective amount of a compound of the formula

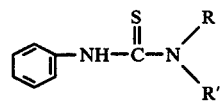

wherein R is hydrogen or methyl; and R' is lower alkyl, allyl, β-hydroxyethyl, β-aminoethyl, ω-aminohexyl, a fatty acid radical, methoxyphenyl, chlorophenyl, phenyl, benzyl, tolyl, hydroxyphenyl, carboxyphenyl, chinoyl, carboxyhydroxyphenyl, hydroxynitrophenyl, nitrophenyl, hydroxychlorophenyl, chloronitrophenyl, phenylthioureidohexyl, trimethylphenyl, methylchlorophenyl, pyridyl, acetylphenyl, acetylaminophenyl, dimethylaminophenyl, aminopyridyl, phenylthioureidopyridyl, phenylthioureidonaphtyl, aminonaphthyl, chlorophenylthioureidophenyl, furfuryl, dichlorophenyl or allylthioureidophenyl. The compound may be administered orally, preferably in dosages of from 40 to 200 mg per kilogram body weight.

1 Claim, No Drawings

METHOD FOR TREATING A PICORNA VIRUS INFECTION

This application is a continuation of application, Ser. No. 282,918, filed Aug. 23, 1972, now abandoned.

BACKGROUND OF THE INVENTION

Considerable research has been conducted in the area of finding compounds possessing antiviral activity. This has become a subject of major research in the field of virology, being directly concerned with the prophylaxis and particularly the treatment of diseases caused by viral infections.

The antiviral properties of the thiourea derivatives and of the structurally related to them thiocarbanilides were first proved by Buu-Hoi. By carrying out tests on mice these substances showed a certain effect on the type A/PR8 of the influenza virus. Girard et al. found that some dithiobiuret derivatives could protect mice inoculated with poliovirus 2. Well known with their considerable antiviral acitivity are also the N-methylizatine-$\beta$-thiosemicarbazone derivatives which found wide application in smallpox prophylaxis.

It is an object of the present invention to provide active antiviral compositions.

SUMMARY OF THE INVENTION

In accordance with the invention, it has been discovered that picorna virus infections may be treated with a thiourea of the formula:

$$\text{C}_6\text{H}_5\text{—NH—C(=S)—N(R)(R')} \quad (I)$$

wherein
R is hydrogen or methyl; and
R' is lower alkyl, allyl, $\beta$-hydroxyethyl, $\beta$-aminoethyl, $\omega$-aminohexyl, a fatty acid radical, methoxyphenyl, chlorophenyl, phenyl, benzyl, tolyl, hydroxyphenyl, carboxyphenyl, chinolyl, carboxyhydroxyphenyl, hydroxynitrophenyl, nitrophenyl, hydroxychlorophenyl, chloronitrophenyl, phenylthioureidohexyl, trimethylphenyl, methylchlorophenyl, pyridyl, acetylphenyl, acetylaminophenyl, dimethylaminophenyl, aminopyridyl, phenylthioureidopyridyl, phenylthioureidonaphthyl, aminonaphthyl, chlorophenylthioureidophenyl, furfuryl, dichlorophenyl or allylthioureidophenyl. The thiourea compounds (I) are preferably administered in dosages of 40 to 200 mg/kg. The thiourea compounds (I) may be administered orally, such as in powder form, granules, an aqueous suspension, an emulsion, tablet or other conventional means.

DETAILED DESCRIPTION OF THE INVENTION

The thiourea compounds (I) are prepared by methods known in the art. (Some of the thiourea compounds (I) are known, particularly as being useful in herbicidal compositions.) A convenient method for their synthesis following a reaction known in the art is the treatment of phenylisocyanate with an amine of the formula

HNRR' wherein R and R' are as defined above. The reaction is conducted in an organic solvent.

Unexpectedly, it has been discovered that the thiourea compounds (I) show high antiviral activity for picornaviruses [polio, Coxsackie A and B, ECHO and the foot-and-mouth (FMD) virus]. The inhibiting action on the multiplication of poliovirus 1, coxsackie virus B1, echovirus 19 and FMD virus is estimated at 95.0 to 99.9%. Marked antiviral activity is also registered when the said thiourea compounds (I) are applied on experimental Coxsackie A6, A7, B1 and B3 infections, as well as on experimental foot-and-mouth disease. The thiourea compounds (I) are applied in doses of 40–200 mg/kg at high values (above 5) of the selectivity index (acute toxicity 400 – 1000 mg/kg).

EXAMPLES 1–11

The antiviral activity of the thiourea compounds (I) is tested on the following picornaviruses: polio virus 1, coxsackievirus B1, exhovirus 19 and FMD virus type C, by the following methods:

1. Screening gradient plaque-inhibition test of Kucera and Herrmann modified in the Viral Inhibitors' Laboratory of the Department of Virology, Postgraduate Medical Institute, Sofia.
2. One-step virus growth cycle experiments.

The gradient plaque-inhibition test is carried out on monolayer cell cultures in "Povitzky" flasks (FL cells used for poliovirus 1, coxsackievirus B1 and echovirus 19; calf kidney primary cultures for the FMD virus), said monolayer cultures being inoculated with 200–300 plaque-forming units (PFU) of the corresponding virus. Two layers of agar cover are placed in such a way as to form gradient in the concentration of the tested substance, contained in the second layer. After a 48 hour incubation period, the antiviral effect is measured by the presence of a zone, close to the toxic one, not containing plaques or containing plaques with reduced diameter.

When carrying out one-step virus growth cycle experiments, monolayer cultures of the types shown in "Brosse" flasks are inoculated at high multiplicity of infection (above 50 for poliovirus 1, coxsackievirus B1 and echovirus 19; and above 20 for the FMD virus). The tested compounds used at maximum subtoxic concentration are placed in maintaining solution. At the end of the virus growth cycle (taking 8 to 9 hours) and after trifold freezing and thawing the virus yield with each of the tested compounds is measured. The percentage inhibition is estimated using a control sample for comparison.

The activity of the said derivatives in vivo is illustrated by experimental inoculation of newborn mice using coxsackievirus A and B (5–10 $LD_{50}$ virus dose subcutaneously inoculated) and FMD in guinea pigs (5–15 $ID_{50}$ virus dose by foot-pad inoculation). The compounds are subcutaneously administered once daily and the effect on the infection challenge and on the course of the experimental Coxsackie or FMD infections are estimated on the base of the percentage of lethality in the treated animal groups, in comparison to the placebo group, and on measuring the alternative responce time: $ET_{50}$ $ET_{50}$(Link, 1968). When carrying out tests on guinea pigs by inoculating them with FMD virus the the effect shown by the compounds of the present invention is measured on the base of the percentage of animals in the treated animal groups showing generalized infection, compared with the placebo group.

The results from testing the antiviral activity of some of the thiourea compounds (I) towards the poliovirus are tabulated below:

Action of some derivatives of N-phenyl-N'-alkylthiourea and N-phenyl-N'-arylthiourea on the multiplication of poliovirus 1

| Ex. | Thiourea Compounds (I) | Results from the gradient plaque-inhibition test | Results from the one-step virus growth cycle experiments | |
|---|---|---|---|---|
| | | | PFU/ml | % of inhibition |
| 1 | 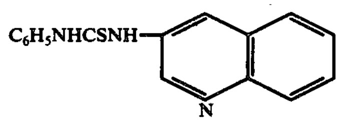  | + | $3.3 \times 10^8$ | 67.00 |
| 2 | 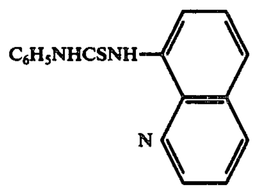  | + | $5.2 \times 10^8$ | 48.00 |
| 3 | 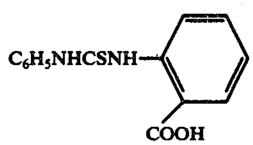  | +++ | $5.9 \times 10^7$ | 95.09 |
| 4 | 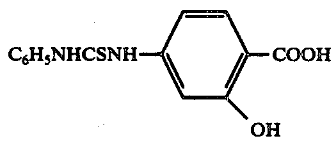  | ++ | less $1 \times 10^6$ | more 99.92 |
| 5 | 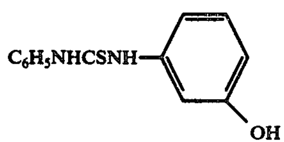  | ++ | $7 \times 10^6$ | 99.42 |
| 6 | 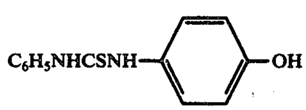  | ++ | $3.7 \times 10^8$ | 69.17 |
| 7 | 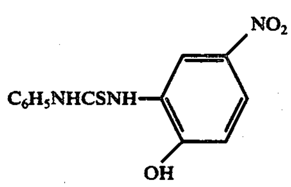  | ++ | $3.5 \times 10^8$ | 70.83 |
| 8 | $C_6H_5NHCSNHCH_2CH_2CH_2COOH$ | ++ | $1.5 \times 10^7$ | 98.75 |
| 9 | 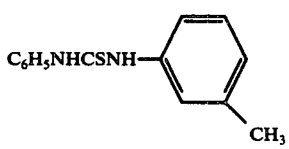  | ++ | $1.4 \times 10^7$ | 98.79 |
| 10 | 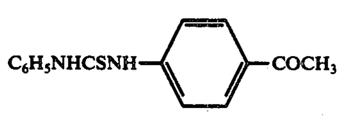  | ++ | $4.6 \times 10^7$ | 96.17 |

-continued

Action of some derivatives of N-phenyl-N'-alkylthiourea and
N-phenyl-N'-arylthiourea on the multiplication of poliovirus 1

| Ex. | Thiourea Compounds (I) | Results from the gradient plaque-inhibition test | Results from the one-step virus growth cycle experiments | |
|---|---|---|---|---|
| | | | PFU/ml | % of inhibition |
| 11 | 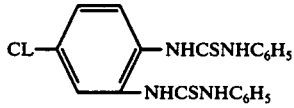 | + | $4.3 \times 10^8$ | 57.00 |
| Control sample | | | $1.2 \times 10^9$ | |

As seen from Examples 1–11 the antiviral acitivity of some of the thiourea compounds (I) is extremely high. For example, N-phenyl-N'-4-carboxy-5-hydroxyphenylthiourea used in concentration of 40 μg/ml inhibits 99.92% of the virus yield; N-phenyl-N'-3-hydroxyphenylthiourea in concentration of 20 μg/ml — 99.62%. High activity is also manifested by the following compounds: N-phenyl-N'-3-tolylthiourea, μ-phenylthioureidobutyric acid, N-phenyl-N'-acetylphenylthiourea and N-phenyl-N'-2-carboxyphenylthiourea, which inhibit 95–99% of the virus yield.

EXAMPLES 12–16

The antiviral activity for the coxsackievirus B1 of some thiourea derivatives was tested. A high inhibiting effect is manifested when using N-phenyl-N'-4-carboxy-5-hydroxyphenylthiourea, N-phenyl-N'-3-hydroxyphenylthiourea, N-phenyl-N'-4-hydroxyphenylthiourea and γ-phenylthioureidobutyric acid. The inhibiting effect is estimated at 99.87% of the virus yield. The results of the tests are tabulated below.

Action of some derivatives of N-phenyl-N'-alkylthiourea and
N-phenyl-N'-arylthiourea on multiplication of coxsackievirus B1

| Ex. | Thiourea Compounds (I) | Results from the gradient plaque-inhibition test | Results from the one-step virus growth cycle experiments | |
|---|---|---|---|---|
| | | | PFU/ml | % of inhibition |
| 12 | 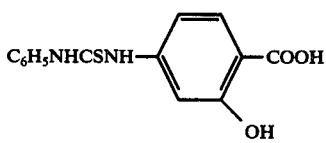 | + | $\leq 1 \times 10^6$ | $\geq 99.87$ |
| 13 | 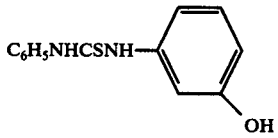 | + | $\leq 1 \times 10^6$ | $\geq 99.87$ |
| 14 | 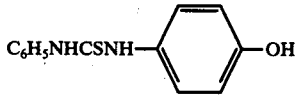 | +++ | $< 1 \times 10^6$ | $> 99.87$ |
| 15 | 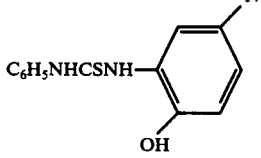 | ++ | $4.6 \times 10^7$ | 93.87 |
| 16 | $C_6H_5NHCSNHCH_2CH_2CH_2COOH$ | + | $\leq 1 \times 10^6$ | $\geq 99.87$ |
| Control sample | | | $7.5 \times 10^8$ | |

Examples 17–21

The antiviral activity of some of the thiourea compounds (I) on echovirus 19 was tested with the following results:

Action of some derivatives of N-phenyl-N'-alkylthiourea and
N-phenyl-N'-arylthiourea on the multiplication of echovirus 19

| Ex. | Thiourea Compounds (I) | Results from the gradient plaque-inhibition test | Results from the one-step virus growth cycle experiments | |
|---|---|---|---|---|
| | | | PFU/ml | % of inhibition |
| 17 | $C_6H_5NHCSNH$—(phenyl with COOH) | ++ | $5 \times 10^6$ | 99.81 |
| 18 | $C_6H_5NHCSNH$—(phenyl with COOH and OH) | ++ | $< 1 \times 10^6$ | $> 99.96$ |
| 19 | $C_6H_5NHCSNH$—(phenyl with OH) | ++ | $2 \times 10^6$ | 99.92 |
| 20 | $C_6H_5NHCSNH$—(phenyl with $NO_2$ and OH) | ++ | $5.9 \times 10^7$ | 97.73 |
| 21 | $C_6H_5NHCSNHCH_2CH_2CH_2COOH$ | +++ | $5 \times 10^6$ | 99.81 |
| Control sample | | | $2.6 \times 10^9$ | |

It is clear from the table that high antiviral activity (inhibition of the virus yield above 99%) is registered with the following thiourea derivatives: N-phenyl-N'-4-carboxy5-hydroxyphenylthiourea, N-phenyl-N'-3-hydroxyphenylthiourea, N-phenyl-N'-2-carboxyphenylthiourea and μ-phenylthioureidobutyric acid. Marked antiviral properties are also observed with the N-phenyl-N'-2-hydroxy-5-nitrophenylthiourea (97.73% inhibition of the virus yield).

EXAMPLES 22–23

The antiviral activity of some thiourea compounds (I) on FMD virus were tested:

Action of some derivatives of N-phenyl-N'-alkylthiourea and
N-phenyl-N'-arylthiourea on the multiplication of the FMD virus type C

| Ex. | Thiourea Compounds (I) | Results from the gradient plaque-inhibition test | Results from the one-step virus growth cycle experiments | |
|---|---|---|---|---|
| | | | PFU/ml | % of inhibition |
| 22 | $C_6H_5NHCSNH$—(phenyl with OH) | + | $1.5 \times 10^5$ | 97.92 |
| 24 | $C_6H_5NHCSNH$—(phenyl)—OH | ++ | $2.5 \times 10^4$ | 99.65 |
| Control sample | | | $7.2 \times 10^6$ | |

High activity is manifested by N-phenyl-N'-4-hydroxyphenylthiourea — 99.65% inhibition of the virus yield. N-phenyl-N'-3-hydroxyphenylthiourea inhibits 97.92% of the virus yield. The N-phenyl-N'-4-carboxy-5-hydroxyphenylthiourea and the N-phenyl-N'-3-hydroxyphenylthiourea marked antiviral activity when tested on experimentally infected with coxsackievirus B1, B3, A6 and A7 (3–10 $LD_{50}$) newborn mice. The course of the infection is retarded by 2–3 days and survival of 50 to 70% of the tested animals is observed. The $ED_{50}$ dose of N-phenyl-N'-40carboxy-5-hydroxyphenylthiourea is 43.3 mg/kg, and that of N-phenyl-N'-3-hydroxyphenylthiourea is 86.6 mg/kg, these being subcutaneously applied once daily during the period starting 48 hours before viral inoculation and lasting throughout the complete course of the disease.

In cases of experimental infection in newborn mice (5–10 $LD_{50}$ virus dose) the daily application of 86.6 mg/kg of N-phenyl-N'-4-hydroxyphenylthiourea according to the above schedule results in survival of 84.6 to 100% of the treated animals, whilst the percentage of lethality in the placebo group is 90 to 100%. N-phenyl-N'-3-hydroxyphenylthiourea applied in dose of 173.2 mg/kg (acute toxicity 1000.0 mg/kg) prevents development of FMD encephalitis in 33.3% of the inoculated with 10 $LD_{50}$ virus dose animals (compared with 100% lethality in the placebo group).

In cases of experimental FMD with guinea pigs (5–15 $ID_{50}$) the compound of Example 23 when applied in 40–60 mg/kg daily doses for a period starting 48 hours before the virus inoculation and continuing for 5 days after the inoculation reduces the number of ailing animals two to three and a half times as compared with the placebo group (significance level p less than 0.01).

When investigating the acute toxicity for mice and rats of N-phenyl-N'-4-carboxy-5-hydroxyphenylthiourea the following $LD_{50}$ values were determined (estimated by the Pershin method): for mice — 550.1 mg/kg (intraperitoneal application) and more than 1000.0 mg/kg (subcutaneous application); for rats — 733.6 mg/kg (intraperitoneal application). It is obvious that this compound possesses high selectivity index ($LD_{50}/ED_{50} \geq 23$).

When tracing the subacute toxicity of compound N-phenyl-N'-4-carboxy-5-hydroxyphenylthiourea for rats with the compound being intraperitoneally applied in 200 mg/kg daily doses for the duration of 30 days, no changes in the general state and behaviour of the animals, or in their weight, the blood pattern, etc. were observed. No teratogenic effect was noted when treating pregnant female rats this compound (intraperitoneal daily doses of 100 mg/kg).

What is claimed is:

1. A method of treating a picorna virus infection which comprises orally administering to a patient an anti-picorna virus effective amount of N-phenyl-N-4-hydroxy-phenylthiourea or N-phenyl-N-3-hydroxyphenylthiourea.

* * * * *